United States Patent [19]

Lay et al.

[11] 4,451,453

[45] May 29, 1984

[54] METHOD FOR TREATING CONTACT DERMATITIS

[75] Inventors: George E. Lay, Fountaintown, Ind.; Daniel H. Haigh, Sanford, Mich.

[73] Assignee: The Dow Chemical Company, Midland, Mich.

[21] Appl. No.: 367,844

[22] Filed: Apr. 13, 1982

[51] Int. Cl.$^3$ .............................................. A61K 31/78
[52] U.S. Cl. ..................................................... 424/81
[58] Field of Search ......................................... 424/81

[56] References Cited

U.S. PATENT DOCUMENTS

| | | | |
|---|---|---|---|
| 3,322,695 | 5/1967 | Alfrey et al. | 260/2.5 |
| 3,520,806 | 7/1970 | Haigh | 210/40 |
| 3,615,972 | 10/1971 | Morehouse et al. | 156/79 |
| 3,750,688 | 8/1973 | Hall et al. | 137/2 |
| 3,849,576 | 11/1974 | Kalopissis | 424/330 |
| 3,953,406 | 4/1976 | Marsh | 260/77.5 AM |
| 3,976,781 | 8/1976 | Kalopissis | 424/309 |
| 4,039,489 | 8/1977 | Fletcher | 260/2.5 AD |
| 4,071,670 | 1/1978 | Vanzo et al. | 526/88 |
| 4,112,067 | 9/1978 | Tomalia et al. | 424/78 |
| 4,186,191 | 1/1980 | Chamberlin et al. | 424/78 |

Primary Examiner—Leonard Schenkman

[57] ABSTRACT

Contact dermatitis caused by exposure of the skin to the allergen present in plants of the genus Rhus, is treated and controlled by topical application of an effective amount of an allergen-imbibing, allergen-retaining polymer or a pharmaceutically-acceptable composition containing such polymer.

7 Claims, No Drawings 4,451,453

METHOD FOR TREATING CONTACT DERMATITIS

BACKGROUND OF THE INVENTION

Contact dermatitis caused by dermal exposure to plant species of the genus Rhus is the most common type of plant-induced dermatitis. Poison ivy (*Rhus toxicodendron radicans*), poison oak (*Rhus toxicodendron diversilobum*), and poison sumac (*Rhus toxicodendron vernix*) all contain allergens consisting of a mixture of 3-substituted catechols. See *J. Am. Chem. Soc.*, 76, 5070 (1954).

During the allergic sensitization process, the allergens assume haptene configurations, and combine with epidermal proteins to form complete antigens on conjugated proteins. Each conjugate leaves the skin via the lymphatic system and is carried to the reticuloendothelial system where special antibodies are synthesized in response to the antigenic stimulus of the conjugate. The antibodies enter the blood stream and are transmitted to the entire cutaneous system where they become fixed, establishing a generalized state of cutaneous sensitization. See, *Handbook of Non-Prescription Drugs*, (pp. 172-175), published by The American Pharmaceutical Association (1973).

SUMMARY OF THE INVENTION

This invention relates to a method of controlling and treating dermatitis in a person who has been exposed to the allergen produced by plants of the genus Rhus which comprises the topical application of an effective amount of an uncrosslinked or a lightly crosslinked copolymer which removes the allergen from the skin surface and underlying dermal tissue. By applying the polymer to the affected area, the allergen is effectively drawn to and taken up by the polymer, and can then be removed without spreading the allergen to unaffected areas of the body.

In the method of the present invention the copolymer utilized must be one which is capable of imbibing and retaining the allergen from the skin surface and adjacent underlying dermal tissue. It is critical that the copolymer utilized be contacted with all portions of the skin exposed to the allergen.

The pharmacologically-acceptable allergen-imbibing, allergen-retaining polymers which may be employed in the method of the present invention comprise uncrosslinked or lightly crosslinked copolymers of for example, isobornyl acrylate, isobornyl methacrylate, styrene, or alkylstyrenes (preferably tertiary alkylstyrenes wherein the alkyl groups contain from 4-12 carbon atoms) and one or more alkyl ester of a $C_1$ to $C_{20}$ alcohol and acrylic or methacrylic acid. The alkylstyrene can be, for example, 4-tert-butylstyrene, 4-tert-amylstyrene, 3,5-ditert-butylstyrene, 4-tert-hexylstyrene, 4-tert-octylstyrene or 4-tert-dodecylstyrene. Tertiary butylstyrene (4-tert-butylstyrene, "TBS") is the preferred alkylstyrene. The alkyl ester monomers can include for example, butyl methacrylate, butyl acrylate, hexyl acrylate, 2-ethylhexyl acrylate, cetyl methacrylate, eicosyl acrylate, the mixed ester cetyl-eicosyl methacrylate, lauryl methacrylate, stearyl methacrylate, and lauryl acrylate. The alcohol moiety of the ester is preferably of from about 8 to about 20 carbon atoms, and is preferably a linear fatty alcohol residue such as cetyl, lauryl, stearyl or eicosyl, or a secondary alcohol residue.

The copolymer may contain from about 5 to about 95 percent alkystyrene monomer by weight. Preferably, the copolymer may contain from about 60 to about 85 to 90 percent by weight of the alkylstyrene. The alkyl ester monomer preferably includes one or both of a methacrylate ester and/or an acrylate ester of one or more $C_8$ to about $C_{20}$ fatty alcohols, or a $C_{10}$ to about $C_{20}$ fatty alcohol methacrylate or acrylate as essentially the sole comonomer.

The copolymer may be uncrosslinked or lightly crosslinked with a minor amount of a crosslinking agent, sufficient to insure that the polymer will not be soluble in or miscible with oils present in the skin. Too much crosslinking may hinder or prevent the polymeric particles from imbibing the allergen. In general, the preferred polymers can contain from about 0.001 to about 0.1 percent by weight of a crosslinking agent (based on a total weight of the alkylstyrene and the alkyl ester monomers). Preferably, about 0.01 to about 0.05 to about 0.075 percent of crosslinking agent is employed. The crosslinking agent can be any di- or polyfunctional compound known to be useful as a crosslinking agent in polymeric vinyl addition compositions, such as divinylbenzene, vinyl isopropenyl benzene, butadiene, or other polyethylenically unsaturated crosslinking agents described, for example, in U.S. Pat. No. 3,520,806. Divinylbenzene is preferred as a crosslinking agent, in amounts from about 0.025 to about 0.05 to about 0.075 to about 0.1 weight percent.

In general, for a given amount of polymer administered, the contact with the allergen and the rate of allergen absorption is enhanced as the ratio of surface area to weight of the polymer increases. Thus smaller particles, with diameters such as from about 100-500 Angstrom units to about 5 microns generally imbibe more rapidly and are generally more effective on a weight basis, than particles of from about 5-50 microns in diameter, which are, in turn, more effective than particles in the 50 micron to 1-2 millimeter range, and so on up to the maximum size conveniently administerable.

In some instances, it may be desirable for the particles to be sufficiently small to form a stable aqueous dispersion. However, particles with an average diameter of about 30 to 60 microns or greater are difficult to maintain in aqueous suspension.

The polymer particles must also be of sufficient size to prevent passage of significant amounts of particles through the skin thereby avoiding the consequent distribution of particles in other parts of the body, such as the blood stream. In general, all the particles should be greater than about 40 to about 50 Angstrom units in their smallest dimension and desirably at least 1000 Angstrom units wide at their smallest dimension. It is convenient to employ generally spherical particles which have diameters of at least about 0.05 to about 20 microns. It is preferred to employ such particles with diameters of from about 0.5 to about 20 microns.

The small particles may be prepared by a variety of known methods such as grinding, milling, cutting or comminuting extruded strands of polymer, or by emulsion or suspension polymerization techniques. Various suitable techniques are disclosed in U.S. Pat. Nos. 3,615,972 and 4,071,670. Suspension polymerization is a well-known process for forming polymer particles with spherical or bead-like configuration and relatively uniform particle size, and this technique can be conveniently employed to make the polymers.

The polymers are preferably, but not necessarily, prepared by emulsion or suspension polymerization of the monomers (and crosslinking agent) in an aqueous emulsion or aqueous suspension. In emulsion polymerization, the polymerization occurs in micelles formed by the monomer mixture and the emulsifier. In the suspension technique, polymerization occurs in monomer droplets suspended in the aqueous phase. Suspension polymerization is preferred for making larger particles, e.g. from about 0.3 to about 0.5 micron and larger.

The polymerization reaction proceeds at temperatures from about 50° to about 120° C., conveniently from 70° to 90° C., and in the presence of a minor amount (typically from about 0.5 to about 10 times the amount of the crosslinking agent) of a polymerization initiator such as potassium persulfate or tertiary-butyl peroctoate. In preparing the copolymers, the monomers and crosslinking agent are mixed together in the proportions corresponding to those desired for the product, then dispersed in water containing either an emulsifying agent or a suspending agent. The proportions are preferably selected so the monomer plus crosslinking agent comprise about 20 to about 60 percent by weight of the aqueous mixture. The polymerization initiator is mixed with either the monomer mixture or the aqueous phase depending on the polymerization method, the initiator used and its relative solubility in the two phases. The mixture is then mixed in order to disperse the monomer phase in the aqueous phase, and to reduce the particle size of the mixture of monomer and crosslinking agent to the size desired for suspension polymerization; and to form micelles of the desired size for emulsion polymerization. The resulting mixture is heated with stirring at a temperature in the polymerization temperature range until the reaction is substantially complete (generally about 4 to about 24 hours). The copolymer product can be recovered and worked up by conventional techniques such as filtration or screening to remove any coagulum or large-particle waste, dialysis, lyophilization or, particularly, with polymer particle sizes on the order of 0.15 micron and larger, by filtration to separate the reaction medium, alcohol precipitation, washing with lower alkanols, steam distillation or other known techniques.

In a convenient purification procedure for polymer particles prepared by suspension polymerization, the suspension is passed through a screen to remove all large coagulum waste particles, then mixed with about 10 parts by volume of isopropanol. The particles are allowed to settle, and the supernatant liquid removed by decantation. Washing with isopropanol can be repeated, if desired. The washed polymer particles can be separated by conventional techniques such as decantation, centrifugation, evaporation, or filtration. The washed particles can be used directly or suspended in an aqueous carrier.

Purification is preferably achieved by isolating the material as a filter cake and then sequentially washing the intact filter cake with deionized water and then an alcohol such as, for example, 95 percent ethanol or isopropanol, under pressure.

In practicing the method of the present invention, an effective amount of the polymer or polymeric composition is applied topically to the skin where exposure to the allergen occurred. As used herein, the term "effective amount" refers to the amount of polymer or polymeric composition sufficient to cause a significant decrease in the severity of the dermatitis or sufficient to prevent or delay the development of the dermatitis. The polymer or polymeric composition may be applied following exposure to prevent or control the development of dermatitis, or the polymer or polymeric composition may be applied after the dermatitis has developed to prevent further spread of the dermatitis and to soothe the existing irritation. The polymers or polymeric compositions can be administered in any pharmaceutically-acceptable form, that is, in any physical form in which the polymer can be conveniently contacted with the affected area of the skin, but which does not cause significant irritation of the skin. Preferably, the polymers described herein are employed in the form of small particles, such as granules, powders, beads, or small spherical particles (see, e.g., U.S. Pat. No. 3,615,972) in combination with a pharmaceutically-acceptable carrier in suitable form for topical application. The polymers described herein may also, in an appropriate solvent system, be incorporated into pharmaceutical compositions suitable for topical application. Such compositions exhibit a film-like characteristic upon drying which conveniently prevents the spread of the allergen and facilitates removal of the composition. Such polymeric compositions may contain additional physiologically beneficial ingredients, excipients, adjuvants, perfumes, thickeners, stabilizers, and the like. Methods for preparing the pharmaceutically-acceptable polymeric compositions used in the present invention are well known to those skilled in the art. See, for example, *Remington's Pharmaceutical Sciences*, pp. 1461–1762, 13th edition (Mack Publishing Company, 1965) which is incorporated herein by reference. In general, polymeric compositions containing about 5 to about 30 percent polymeric solids may be used. Higher polymer concentrations are also operable but are less esthetically pleasing above the given range.

DESCRIPTION OF SOME PREFERRED EMBODIMENTS

The following examples are set forth as a means of illustrating the present invention. They are specific examples of preferred embodiments, and are not intended as a limitation of the invention.

EXAMPLE 1

10.3 Kilograms (kg) of t-butylstyrene and 5.6 kg of lauryl methacrylate were mixed together. 14.095 Grams (gm) of divinylbenzene crosslinking agent [Divinylbenzene 55, (56.4% active divinylbenzene) The Dow Chemical Company, Midland, Mich. 48640, U.S.A.] and 31.75 gm of t-butyl peroctoate initiator were mixed with the above monomer mixture to form an oil phase mixture. Separately, 685.7 grams of hydroxypropyl methylcellulose (Methocel K-3, The Dow Chemical Company, Midland, Mich. 48640, U.S.A.) was dissolved in 18.6 kg of deionized water to make an aqueous phase mixture.

The oil phase was added to the aqueous phase in a stainless steel drum and agitated to affect a homogeneous dispersion of the oil phase in the aqueous phase. This dispersion was then fed into an in-line homogenizer to reduce the particle size of the monomer droplets. This treatment gave a monomer-in-water stable suspension of 6.25 microns (volume average diameter) droplets.

24.5 Kg of the above suspension was transferred to a reactor. The reactor was sealed and the head space was purged 3 times with nitrogen to insure an inert atmosphere. The reactor was pressurized with nitrogen to 5 pounds per square inch and agitation was begun at 90 revolutions per minute. Hot water was then applied to the reactor jacket and the internal temperature was allowed to rise over a period of approximately 1.5 hours to about 75° C. Temperature and agitation were maintained for about 20 hours, after which the contents were allowed to cool to about 20° C. The reactor contents were then drained through a 40-mesh screen into a suitable container.

Solids determination showed the polymer to be about 46 percent of the reactor effluent, and the particle size of the polymer was found to be 5.52 microns (volume average diameter) representing about 99 percent recovery.

EXAMPLE 2

In order to test the effectiveness of the method of the present invention, the following procedure was performed.

(a) Materials

(1) Polymer Composition

A copolymer consisting of t-butylstyrene (about 65%) and laurylmethacrylate (about 35%) lightly cross-linked with about 0.05% divinylbenzene was prepared in accordance with the method of Example 1. Four compositions were prepared containing one of four concentrations of the polymer described above (i.e. 5, 10, 20, or 25 percent polymer) in admixture with carbomer (carboxypolymethylene), sodium stearate, isopropyl alcohol, and water.

(2) Artificial Sebum

A mixture representing the major components of human sebum was prepared by admixing the constituents in the following proportions (percent by weight):
Cholesterol: 2.5
Oleic acid: 25.0
Triolein: 30.0
Cetyl palmitate: 25.0
Cholesterol oleate: 2.5
Squalene: 15.0

(3) Pentadecylphenol Solution

3-Pentadecylphenol (PDP),

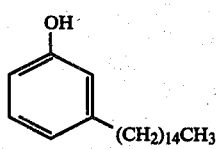

is structurally similar to the allergen present in plants of the genus Rhus. That allergen is a combination of 3-substituted catechols wherein the substituent at the 3-position is a 15-carbon, unbranched, unsubstituted side chain which may be saturated or exhibit various degrees of unsaturation. See, *J. Org. Chem.*, 24, 980 (1959). The use of PDP to induce Rhus-like dermatitis is well-known in the art and the evidence of cross-sensitization between mono or di-hydroxy phenols and the Rhus allergen has been established. See for example, Kligman, A., "Poison Ivy (Rhus) Dermatitis—An Experimental Study", *Archives of Dermatology* (The American Medical Association), Vol. 77, pp. 149–180 (Feb. 1958) which is incorporated herein by reference.

For the procedure described herein, PDP (10 milligrams) was dissolved in a small amount of hexane. This solution was then added to the artifical sebum previously described.

(b) Procedure

One ml of the artificial sebum-PDP mixture (containing 10 mg/ml of the artificial sebum and 10 mg/ml of PDP in hexane) was pipetted into a 50 ml round-bottom flask. The flask was swirled under nitrogen to remove the hexane, which also conveniently coated the lower half of the flask with the artificial sebum-PDP mixture. An amount of polymer composition sufficient to coat the lower two-thirds of the flask was added. The flask was then placed in a 37° C. oven for 40 minutes. The contents of the flask were then removed by washing with three separate 2 ml portions of water. The water washes were collected and the PDP was extracted with 10 ml of hexane. The hexane extracts were then analyzed to determine the amount of PDP recovered from the polymer composition.

In order to insure that a statistically significant quantity of free PDP (i.e., not absorbed by the polymer) was not removed by the water washes, a control was employed wherein no polymer was added to the composition previously described. Any quantity of PDP removed by the water washes in the control was subtracted from the quantities recovered from the polymer compositions.

(c) Results

The results of this procedure are set forth in Table 1 below.

TABLE 1

| % Polymer In Composition | Amount of PDP Absorbed[1] | % PDP Absorbed[2] |
|---|---|---|
| 5% | 6.0 mg | 60% |
| 10% | 5.6 mg | 56% |
| 20% | 4.9 mg | 49% |
| 25% | 5.4 mg | 54% |

[1]Quantity indicated represents the amount of PDP recovered from the polymer composition less the amount of PDP recovered in the control.
[2]10 mg of PDP present in a sebum-coated flask.

EXAMPLE 3

Following a procedure substantially the same as that described in Example 2 above, dose response data was obtained for the 20 percent polymer composition prepared above. A given quantity of polymer composition (i.e., 0.5, 1.0, 1.5, 2.0, or 2.5 ml) was added to each of five separate sebum-coated flasks, each of which had 20 mg of PDP available for absorption. A control was utilized as described in Example 2. The results of this procedure are set forth in Table 2 below.

TABLE 2

| (20% Polymer Composition) | |
|---|---|
| Amount of Polymer Composition Added | Amount of PDP Absorbed[1] |
| 0.5 ml | 19.1 mg |
| 1.0 ml | 20.0 mg |
| 1.5 ml | 20.0 mg |
| 2.0 ml | 20.0 mg |

TABLE 2-continued (20% Polymer Composition)

| Amount of Polymer Composition Added | Amount of PDP Absorbed[1] |
|---|---|
| 2.5 ml | 20.0 mg |

[1] 20 mg of PDP present in a sebum-coated flask. The quantity indicated represents the amount of PDP recovered from the polymer composition less the amount of PDP recovered from the control.

EXAMPLE 4

Two polymer formulations (A and B) were prepared for use in a test on rabbits. Each of Formulations A and B contained 200 mg/gm of the polymer described in Example 1. Formulation A was composed of the polymer admixed with carbomer, sodium stearate, isopropyl alcohol and water. The polymer was admixed with isopropyl alcohol and water in Formulation B. A third formulation, Formulation C, (a placebo) consisted of carbomer, sodium stearate, isopropyl alcohol and water, without the addition of the polymer.

The backs of each of three previously shaven and prepared white rabbits were marked into four test quadrants. To each of the four quadrants was applied 1 ml of a 1 mg/ml solution of PDP in acetone which was allowed to remain in contact with the skin for 30 minutes.

One quadrant on each animal was used as a control, (to which none of the formulations was added), and each of the other three quadrants was designated to receive 1 gm each of either Formulation A, B, or C (placebo). The application to each quadrant were allowed to remain on the skin for 1 hour after which they were physically removed and collected in such a manner as to keep the collected material from each quadrant in a separate receptacle. Each quadrant was then rinsed with two 5 ml portions of water and wiped with gauze sponges. The water washes and sponges were also collected as described above. After one hour, the aforementioned application and collection procedure was repeated. The collected samples from each quadrant were combined, extracted with hexane and assayed for PDP.

The results of this test are set forth in Table 3, below.

TABLE 3

(Percent Recovery of 1.0 mg PDP Per Test Quadrant)

| Test Quadrant | Animal No. 1 | Animal No. 2 | Animal No. 3 |
|---|---|---|---|
| Control | 4.3 | 3.7 | 1.9 |
| Formulation A | 35.5 | 49.5 | 23.5 |
| Formulation B | 33.3 | 46.3 | 23.8 |
| Formulation C[1] | 6.0 | 13.6 | 5.0 |

[1] Formulation C = Placebo

EXAMPLE 5

Following a procedure substantially the same as that described in Example 4, the backs of three rabbits were shaven and prepared as above. One test quadrant on each animal was designated as a control to which 1 ml of a 1 mg/ml solution of PDP in acetone was applied. To the other randomly selected test quadrants was applied one of the following concentrations of PDP in acetone: 0.1, 1.0 or 10 mg. After 30 minutes, one of three concentrations (0.5, 1.0, or 2.0 gm) of Formulation A (as described in Example 4) was applied to randomly selected quadrants such that each quadrant received one of the three concentrations of Formulation A (except those designated as control). The formulation was allowed to remain on each test quadrant for one hour after which it was collected as described in the previous example. The formulation application was repeated, and the collected samples from each quadrant were extracted with hexane and assayed for PDP.

The results of this test are set forth in Table 4, below.

TABLE 4

Percent Recovery of Various Concentrations of PDP Using Various Amounts of Formulation A

| Animal No. | Test Quadrant | Concentration of PDP on the Skin | Amount of Formulation A Applied | Percent Recovery |
|---|---|---|---|---|
| 1 | A | 1.0 mg | Control | 17.3 |
| 1 | B | 1.0 mg | 0.5 gm | 28.0 |
| 1 | C | 1.0 mg | 1.0 gm | 28.0 |
| 1 | D | 1.0 mg | 2.0 gm | 51.0 |
| 2 | A | 10.0 mg | 1.0 gm | 28.6 |
| 2 | B | 1.0 mg | 1.0 gm | 46.3 |
| 2 | C | 0.1 mg | 1.0 gm | 100.0 |
| 2 | D | 1.0 mg | Control | 4.0 |
| 3 | A | 0.1 mg | 1.0 gm | 60.0 |
| 3 | B | 10.0 mg | 1.0 gm | 61.7 |
| 3 | C | 1.0 mg | Control | 4.0 |
| 3 | D | 1.0 mg | 1.0 gm | 42.8 |

What is claimed is:

1. A method of controlling and treating dermatitis in humans caused by exposure of the skin to a plant of the genus Rhus which comprises the topical application of an effective amount of an allergen-imbibing, allergen-retaining polymer wherein said polymer is a crosslinked copolymer of isobornyl acrylate, isobornyl methacrylate, styrene, or alkylstyrene and at least one ester of a $C_8$ to $C_{20}$ fatty alcohol with acrylic or methacrylic acid, crosslinked with a polyethylenically unsaturated crosslinking agent.

2. The method of claim 1 wherein the polymer is a copolymer of from about 60 to about 90 percent by weight of a tertiary-alkylstyrene and at least one ester of a $C_8$ to $C_{20}$ fatty alcohol with acrylic or methacrylic acid, crosslinked with from about 0.001 to about 0.1 percent (based on the total weight of said tertiary-alkylstyrene and ester) of a polyethylenically unsaturated crosslinking agent.

3. The method of claim 3 wherein the tertiary-alkylstyrene is tertiary-butylstyrene.

4. The method of claim 3 wherein the crosslinking agent is divinylbenzene.

5. The method of claim 3 wherein the tertiary-alkylstyrene is tertiary-butylstyrene and the ester is a $C_8$ to $C_{20}$ methacrylate.

6. The method of claim 5 wherein the polymer is a copolymer of tertiary-butylstyrene and laurylmethacrylate.

7. The method of claims 1, 2 or 6 wherein the polymer is applied in combination with a pharmaceutically-acceptable carrier in a polymeric composition suitable for topical application.

* * * * *

UNITED STATES PATENT AND TRADEMARK OFFICE
CERTIFICATE OF CORRECTION

PATENT NO. : 4,451,453

DATED : May 29, 1984

INVENTOR(S) : George E. Lay and Daniel H. Haigh

It is certified that error appears in the above-identified patent and that said Letters Patent are hereby corrected as shown below:

Column 7, line 31, "application to each" should read -- applications to each --.

Column 8, line 50, "3. The method of claim 3 wherein" should read -- 3. The method of claim 2 wherein --.

Column 8, line 52, "4. The method of claim 3 wherein" should read -- 4. The method of claim 2 wherein --.

Column 8, line 54, "5. The method of claim 3 wherein" should read -- 5. The method of claim 2 wherein --.

Signed and Sealed this

Eleventh Day of June 1985

[SEAL]

*Attest:*

DONALD J. QUIGG

*Attesting Officer*   *Acting Commissioner of Patents and Trademarks*